United States Patent [19]

Hautmann et al.

[11] Patent Number: 4,844,050

[45] Date of Patent: * Jul. 4, 1989

[54] EVAPORATION APPARATUS FOR ACTIVE INGREDIENTS SUCH AS PYRETHRUM INCORPORATED INTO SOLID CARRIER MATERIALS

[75] Inventors: Horst Hautmann, Neuburg; Bernd Pregler, Glonn; Georg Schimanski, Hagen, all of Fed. Rep. of Germany

[73] Assignee: Globol-Werk GmbH, Fed. Rep. of Germany

[ * ] Notice: The portion of the term of this patent subsequent to Jun. 14, 2005 has been disclaimed.

[21] Appl. No.: 152,529

[22] Filed: Feb. 5, 1988

Related U.S. Application Data

[62] Division of Ser. No. 879,232, May 22, 1986, Pat. No. 4,750,471.

[51] Int. Cl.⁴ ............................................. F24C 5/00
[52] U.S. Cl. ..................................... 126/43; 431/146; 432/222; 126/95; 126/45
[58] Field of Search .................. 432/222; 126/43, 45, 126/95

[56] References Cited

U.S. PATENT DOCUMENTS

| 4,539,973 | 9/1985 | Hait | 126/43 |
| 4,544,348 | 10/1985 | Boij | 126/43 |

Primary Examiner—Henry C. Yuen
Attorney, Agent, or Firm—Townsend and Townsend

[57] ABSTRACT

In order to improve an apparatus for the evaporation of active ingredients such as pyrethrum or similar insecticides, air-improving, bactericidal, disinfecting and/or, for example, curing substances incorporated in cellular boards or other solid carrier materials, consisting of a housing in which there is provided a heating means which is arranged behind a housing window, and of a holding means for the exchangeable arrangement of an active ingredient carrier panel in front of the housing window in such a way that an evaporation apparatus which is independent from electrical energy can be achieved while maintaining high reliability in handling, it is proposed that a catalytic, merely glowing, that is flamelessly acting burner 4 with fuel tank 3 be arranged in the housing 1 having ventilation openings 13 at such a distance from the housing window 2 that the hot waste gases from the burner 4 flow through the housing window 2 and activate the active ingredients.

14 Claims, 1 Drawing Sheet

EVAPORATION APPARATUS FOR ACTIVE INGREDIENTS SUCH AS PYRETHRUM INCORPORATED INTO SOLID CARRIER MATERIALS

This application is a division of application Ser. No. 06/879,232, filed May 22, 1986, now U.S. Pat. No. 4,750,471.

The invention is based on an apparatus for the evaporation of active ingredients such as pyrethrum incorporated in cellular panels or other solid carrier materials, of the type indicated in the preamble to claim 1 and known, for example, from DE-OS No. 3 109 401.

In the apparatus known from DE-OS No. 3 109 401, there is arranged in the housing behind the housing window which is designed approximately the same size as the active ingredient carrier panels, a plate-shaped electric heating means onto which an active ingredient carrier panel is placed in order to be heated to about 100° C. in order to evaporate active ingredients from the heating means.

The electrical heating means is connected inside the housing to outwardly leading plugs by means of which the device can be connected to an electric supply main.

Evaporation apparatuses of this type therefore invariably require an electric heating means.

An object of the invention is accordingly to improve an apparatus of the type indicated in the preamble to claim 1 such that an evaporation apparatus which is independent of electrical energy can be achieved while maintaining at least equivalent reliability in handling and relatively long operating ability as in the past using simple means.

The solution to this problem is characterised in that in the housing containing ventilation openings there is arranged a catalytic, merely glowing, that is flamelessly acting burner with fuel tank at such a distance from the housing window that the hot waste gases from the burner flow through the housing window and activate the active ingredients.

In this way there is obtained an evaporation apparatus which is independent of power distribution networks with which, on the one hand for activating the active ingredients adequate heating is ensured but, on the other hand, despite the use of combustible substances, the risk of fire and furthermore unintentional contact with the burner are ruled out during operation of the evaporation apparatus.

With this arrangement, it is advantageous if the housing window in the housing is arranged vertically above the burner and if erection surfaces securing this position or the like and/or suspension devices are provided on the housing.

A design which simplifies handling of the apparatus is characterised in that the burner and the fuel tank are inserted exchangeably into the housing, the burner and the fuel tank preferably also being combined in one unit.

A further preferred embodiment resides in the fact that the housing, in particular on the side turned away from the housing window, has an opening through which the burner/fuel tank unit is inserted into the housing secured at least by friction, the fuel tank preferably being designed so as to seal the housing opening intended for insertion of the fuel tank.

Consequently, the housing can merely be turned over after ignition of the burner by means of the burner/fuel tank unit without coming into contact with the burner, after which a secure connection between the burner/fuel tank unit and the housing is achieved without further effort.

For this purpose, an advantageous development is characterised in that the fuel tank has a stop which is designed, in particular, in encircling manner and in that a groove cooperating with the stop is arranged in the housing.

A design which improves the effectiveness of the apparatus just described is characterised by a lengthened burner which is arranged running parallel to the base side of the housing on the upper side of the fuel tank, furthermore the housing window is oblong in design and is arranged in the same direction as the length of the burner and guide elements which secure this position are provided on the burner tank and on the housing.

In order further to increase the effectiveness, it is advantageous if there is arranged, in particular shaped, on the upper side of the housing an oblong chamber which is smaller than the housing width and is open towards the burner tank, in whose cover the housing window is provided, furthermore the oblong burner penetrates into the chamber in the same direction as the length of the chamber, furthermore in that the ventilation openings are provided in the lateral walls of the chamber and that finger-width fuel tank discharge openings are arranged next to the chamber in the cover of the housing.

A particularly easily ignitable and at the same time manageable design of the subject just described is characterised by a fuel tank which is filled with liquid fuel, in particular spirit or lighter fuel, in which material which absorbs the liquid fuel is arranged and at least one fuel vaporisation opening directed towards the catalytic burner is provided in the housing, the fuel tank preferably also having a sealable filling opening.

In order further to simplify handling, it is advantageous if a burner ignition device is inserted into the housing.

An embodiment of the invention is illustrated in the drawings and is described in more detail below.

Figure 1:
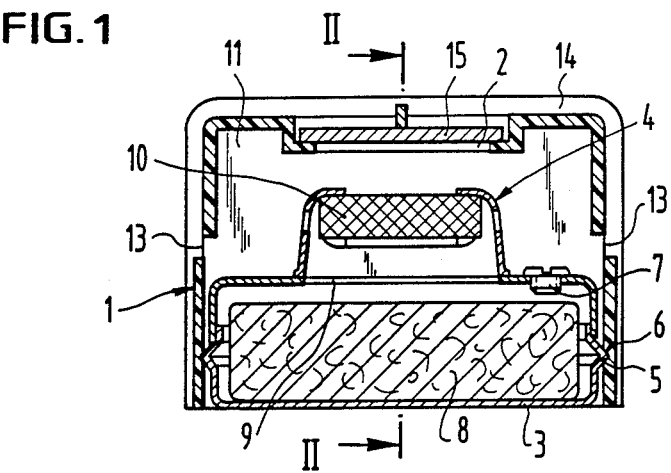
FIG. 1 shows an evaporation apparatus for active ingredients embedded in solid carrier materials in section.

This evaporation apparatus substantially comprises a cylindrical housing 1 which is open at the bottom with a housing window 2 arranged at the top, a fuel tank 3 of flat cylindrical shape and a catalytic oblong burner 4 which is combined to form a unit with the fuel tank 3. The fuel tank is inserted together with burner 4 into the housing 1 which is open at the bottom and is secured against unintentional release by a catch-type connection. For this purpose, a raised stop 5 designed as an encircling bead is shaped on the fuel tank 3 and engages detachably into a groove 6 arranged inside the housing 1. The smooth underside of the fuel tank 3 thus forms with the lower edge portions of the housing 1 the base for the apparatus. In addition, the housing 1 and the fuel tank 3 are designed such that the fuel tank 3 seals the housing 1 which is open at the bottom.

The fuel tank 3 has a filling opening 7 for receiving liquid fuel, in particular spirit or lighter fuel and is filled with absorbent material 8, for example with cotton wool.

A fuel vaporisation opening 9 by means of which the catalytic burner is held is provided in the upper side of the fuel tank 3. This burner 4 consists of an oblong holder 10 composed of porous refractory and gas-permeable material in which solid catalysts, for example finely divided platinum, is arranged. The ends of the holder 10 are fixed in an oblong sheet metal holder which is fixed undetachably on the fuel tank 3.

The oblong burner 4 running parallel to the base side of the apparatus engages in an approximately cuboid chamber 11 which is arranged, in particular shaped, on the upper side of the housing, is open towards the fuel tank 3 and extends diametrally to the housing 1, the lengthwise direction of the burner 4 being arranged in the same direction as the length of the chamber 11.

To permit the prescribed position inevitably to be achieved during insertion of the fuel tank 3 together with burner 4 into the housing 1 or when turning the housing 1 over the burner/fuel tank unit, orientation means, in particular in the form of straight guide elements running parallel to the axis, can be provided on the housing 1 and on the fuel tank 3.

To enable the fuel tank 3 together with burner 4 to be released conveniently from the housing in an intentional manner for the purpose of filling with fuel and/or for igniting the burner, for example with a match, a respective finger-sized opening 12 through which the fuel tank 3 together with burner 4 can be expelled from the housing by the fingers is provided on the upper side of the housing 1 on the two sides of the chamber 11.

Ventilation openings 13 are provided in the narrow walls of the chamber 11. A protective grid 14 and an insertion duct which is open at least at one end for receiving an active ingredient carrier panel 15 in exchangeable fashion is shaped in known manner over the housing window 2 of the chamber 11.

If the fuel tank 3 removed from the housing is filled with fuel and the burner 4 ignited, the housing should be turned by means of the burner/fuel tank unit and only one more active ingredient carrier panel should be positioned above the housing window.

In order further to simplify handling, an ignition device for example in the form of a lighter with friction wheel and flint which can be actuated from the exterior or a piezoelectric ignition device can be inserted into the housing above the burner.

The housing 1 together with chamber 11 and holding device for the active ingredient carrier panel is preferably produced integrally from plastics material while the fuel tank together with burner holder is preferably composed of non-combustible material, in particular of sheet metal.

All new individual features and combined features disclosed in the description and/or drawings are considered as essential to the invention.

The burner 4 used in the evaporation apparatus according to the invention and which can also be described as a catalyst, consists of an approximately cylindrical holder 10, preferably in the form of a wire net in which a fleece, preferably glass fibre fleece, is introduced in such a way that it rests on the interior of the cylindrical wire net. The fleece is thus located in an approximately concentric arrangement relative to the wire net holder 10 in such a way that the fleece defines an approximately cylindrical cavity. The fleece itself is mixed with a catalytic element, preferably platinum. In this way, the gases issuing from the fuel tank 3 enter the interior of the burner 4. The ignition of the gases causes the gases in the region of the burner to produce a glowing operation so that no flame is formed at the burner 4 itself and the heat produced by the glowing of the gases passes directly upwards (FIGS. 1, 2) to the active ingredient carrier panel 15. The heated gases flow past the active ingredient carrier panel 15 and thus cause reinforced volatilization of the active ingredients on the active ingredient carrier panel 15. It is important for the gases produced by the burner 4 to act directly on the active ingredient holder 15; the active ingredient panel 15 is preferably arranged at a distance of from about 8 to 13 mm from the upper edge of the burner 4.

The evaporation apparatus according to the invention therefore has the object of conveying the gases issuing from the fuel tank 3 through the burner 4, allowing them to be heated there and of guiding the heated gases to the active ingredient carrier panel 15 so that the active ingredient carrier panel 15 is heated. To achieve a satisfactory stack effect, i.e. a flow of the heated gases towards the active ingredient carrier panel 15 and past it, the width of the housing window 2 (FIG. 1) is selected greater than the width of the active ingredient carrier panel 15, as shown clearly in FIG. 3, so that the heated gas issues laterally at the active ingredient carrier panel 15 at the upper side of the housing 1. These gases therefore effect not only direct heating of the active ingredient carrier panel 15, but also act as a carrier medium for the active ingredient particles emitted by the panel 15 owing to the heating thereof. The active ingredient particles are entrained by the gases flowing past the panel 15 and are distributed into the surrounding atmosphere. The supply of oxygen to the burner 4 is ensured by the ventilation openings 13 which are formed approximately at the level of the openings 12 or by the openings 12 themselves. It is also important that the slit-shaped opening formed beneath the burner 4 on the upper side of the fuel tank 3 has approximately the same length and width as the burner 4 itself or preferably a narrower slit width than the burner 4. Part of the burner 4 is a holding member which is composed of metal, is designated by 4a in FIG. 2, surrounds the slit-shaped opening of the fuel tank 3 and holds the holder 10 at a small distance above the slit-shaped opening of the fuel tank 3. This holding member 4a ensures that the gases issuing from the opening in the fuel tank 3 pass to the holder 10 and do not escape past the holder 10 into the interior of the housing 1. The width of the holding element 4a (FIG. 2) is preferably approximately equal to the diameter of the holder 10, ensuring optimum supply of the gaseous fuel from the burner tank 3 to the holder 10.

Figure 2:
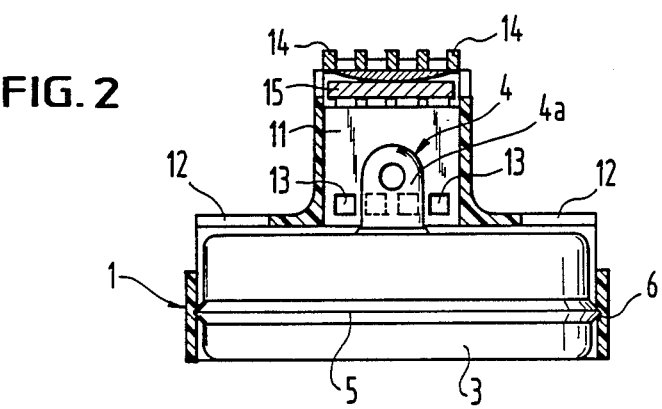
FIG. 2 shows the same in the direction of the line II—II, parts of the apparatus being illustrated in elevation.

In order to keep the distance between the burner 4 and the active ingredient carrier 15 in the operating state of the evaporation apparatus within the necessary range, the housing 1 is staggered in design between the lower portion receiving the fuel tank 3 and the upper portion in which the burner 4 lies, as shown clearly in FIG. 2. The burner 4 is therefore fixed at a distance from the active ingredient carrier 15 by arranging the fuel tank 3 on the step (not shown) located next to the openings 12.

Figure 3:
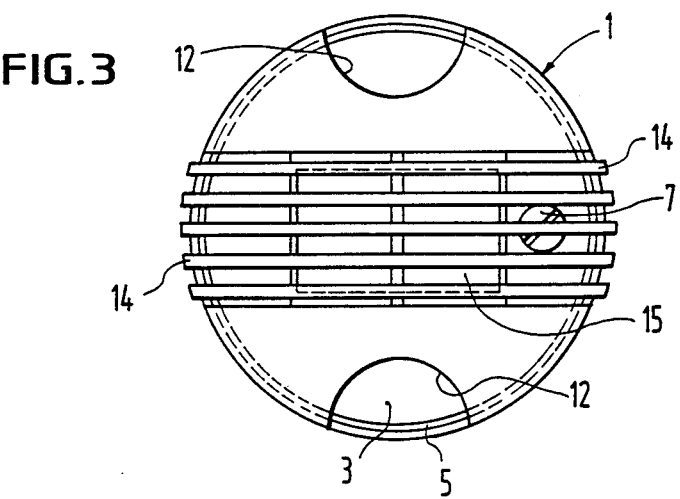
FIG. 3 shows the same, as viewed from above.

A further important feature of the evaporation apparatus described resides in the fact that it is very stable and is substantially secured against tilting or accidental tipping over as a result of the relatively large, for example circular, standing face. As shown in FIGS. 1 to 3, the standing face is defined in part by the circular lower housing portion and the base of the tank 3.

A continuous and steady flow of hot gases to the active ingredient carrier panel 15 and past it is produced by the supply of oxygen by means of the lower ventilation openings 13 and the slits which are defined between the active ingredient carrier panel 15 and the upper side of the housing and act as outlet openings. A flow of hot gases which is directed intentionally from bottom (burner) to the top (panel 15) and is not impaired by the supply of oxygen from the burner, is obtained, i.e. an accumulation or a vortex and cooling of the hot gases possibly associated with the vortex is effectively prevented in the space between the burner 4 and the panel 15.

Finally, the effectiveness during delivery of the active ingredients during operation is optimised with the evaporation apparatus according to the invention. In addition to the directed steady stream of hot gases, the outwardly or upwardly lying face of the active ingredient panel 15 is exposed to the exterior with the exception of the negligibly small surfaces of the supporting ribs 14, so that the active ingredients from the active ingredient panel 15 are delivered to the environment in a substantially unimpaired manner through housing portions etc.

We claim:

1. An apparatus for releasing active ingredients in an active ingredient carrier panel by heating the panel, the apparatus comprising:

a housing having sides, a top, a housing window opening to the exterior, means for allowing the entry of combustion air into the housing, and means for ventilating combustion gas from the housing interior through the window opening to the exterior;

a fuel tank and a flameless catalytic burner forming a heating unit located within the housing and generally beneath the housing window opening;

means permitting the insertion of the heating unit into the housing;

means for releasably retaining the heating unit in the housing to facilitate the rapid replacement of the heating unit with a fresh heating unit;

an active ingredient carrier panel having a surface area less than the surface area of the housing window; and means for replaceably positioning the active ingredient carrier panel above the heating means and across the housing window opening without dismantling the housing;

whereby heated gas generated by the heating means rises within the housing, passes through the housing window and is caused by the shape of the housing to impinge upon the active ingredient carrier panel to thereby heat and release the active ingredients and to carry them with the heated gas to the exterior of the housing.

2. The apparatus of claim 1, wherein said fuel tank includes a horizontally disposed vaporization opening situated generally below said catalytic burner.

3. The apparatus of claim 1, wherein said housing is plastic.

4. An apparatus for releasing active ingredients in an active ingredient carrier panel by heating the panel, the apparatus comprising:

a housing having a bottom, sides, a top, a housing window opening to the exterior, means for allowing the entry of combustion air into the housing, and means for ventilating combustion gas from the housing interior through the window opening to the exterior;

flameless catalytic heating means located within the housing and generally beneath the housing window opening;

means for retaining the catalytic heating means within the housing;

an active ingredient carrier panel having a surface area less than the surface area of the housing window; and means for replaceably positioning the active ingredient carrier panel above the heating means and across the housing window opening without dismantling the housing;

whereby heated gas generated by the heating means rises within the housing, passes through the housing window and is caused by the shape of the housing to impinge upon the active ingredient carrier panel to thereby heat and release the active ingredients and carry them with the heated gas to the exterior of the housing.

5. The apparatus of claim 4, wherein said fuel tank includes a horizontally disposed vaporization opening situated generally below said burner.

6. The apparatus of claim 4, wherein said housing is plastic.

7. The apparatus of claim 4 wherein the heating means comprises a burner and a fuel tank adapted to be exchangeably inserted together into the base of the housing, said fuel tank being positioned below the burner.

8. The apparatus of claim 4 wherein the heating means includes a tank and a burner in fluid communication with the tank, and wherein the housing is tapered at its top and sides to form a chamber of reduced cross section adapted to accommodate the burner.

9. The apparatus of claim 4 wherein the heating means comprises a burner and a fuel tank combined to form one unit.

10. The apparatus of claim 9 wherein the bottom of the housing has an opening through which the burner and fuel tank unit can be inserted into the housing and means for frictionally securing the unit to the housing.

11. The apparatus of claim 10 wherein the fuel tank is shaped to effectively close and seal the opening in the bottom of the housing.

12. The apparatus of claim 4 wherein the panel is disposed exteriorly of the window opening, and including a protective grid extending over the panel and an insertion duct for the panel defined by the housing.

13. The apparatus of claim 4 wherein a bottom surface of the fuel tank forms a support surface for the housing.

14. The apparatus of claim 10 further comprising a burner ignition device extending into the housing.

* * * * *